US00PP23161P3

(12) United States Plant Patent
Slaughter et al.

(10) Patent No.: US PP23,161 P3
(45) Date of Patent: Nov. 6, 2012

(54) PEACH TREE, 'BURPEACHTWENTYSIX'

(50) Latin Name: *Prunus persica*
Varietal Denomination: Burpeachtwentysix

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 65 days.

(21) Appl. No.: 12/928,629

(22) Filed: Dec. 14, 2010

(65) Prior Publication Data

US 2012/0151644 P1 Jun. 14, 2012

(51) Int. Cl.
*A01H 5/00* (2006.01)

(52) U.S. Cl. ..... Plt./198

(58) Field of Classification Search ..... Plt./198, Plt./196
See application file for complete search history.

*Primary Examiner* — June Hwu
(74) *Attorney, Agent, or Firm* — Paine Hamblen, LLP

(57) ABSTRACT

A new and distinct variety of peach tree (*Prunus persica*), which is denominated varietally as 'Burpeachtwentysix', and which produces an attractively colored yellow-fleshed, freestone peach which is mature for harvesting and shipment approximately August 10 to August 17 under the ecological conditions prevailing in the San Joaquin Valley of central California.

1 Drawing Sheet

BACKGROUND OF THE NEW VARIETY

The present invention relates to a new and distinct variety of distinct variety of peach tree, '*Prunus persica*', and which has been denominated varietally as 'Burpeachtwentysix'.

ORIGIN

The present variety of peach tree resulted from an on-going program of fruit and nut tree breeding. The purpose of this program is to improve the commercial quality of deciduous fruit and nut varieties, and rootstocks, by creating and releasing promising selections of *Prunus, Malus* and *Juglans regia* species. To this end we make both controlled and hybrid cross pollinations each year in order to produce seedling populations from which improved progenies are evaluated and selected.

The seedling, 'Burpeachtwentysix' was originated by us and selected from a population of seedlings growing in our experimental orchards located near Fowler, Calif. The seedlings, which were grown on their own roots, were derived from a cross that we made in 2004 of the yellow-fleshed freestone peach identified as E62.012, which was used as the seed parent; and a white-fleshed freestone peach tree identified as E48.050, which was used as the pollen parent. As the fruit ripened the resulting seed from this cross was stratified, germinated, and then was subsequently grown in a greenhouse to an appropriate stage of development. Subsequently, the new plants were field planted, and then grown for further evaluation. One seedling, which is the present variety, exhibited especially desirable characteristics, and was then designated as 'P4.099'. This seedling was then marked for subsequent observation. After the 2006 fruiting season, the new variety of peach tree 'P4.099', now named 'Burpeachtwentysix' was selected for advanced evaluation and repropagation.

ASEXUAL REPRODUCTION

Asexual reproduction of this new and distinct variety of peach tree was accomplished by budding the new peach tree 'P4.099' onto 'Nemaguard' Rootstock (unpatented). This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through these succeeding asexual propagations.

SUMMARY OF THE VARIETY

'Burpeachtwentysix' is a new and distinct variety of peach tree, which is considered of medium to medium large size, and which has a moderately vigorous growth characteristic. This new peach tree is also a regular and productive bearer of relatively large, firm, yellow-fleshed, freestone fruit which have a good flavor and eating qualities. This new peach tree has a medium chilling requirement of approximately 550 hours, and further produces relatively uniformly sized fruit throughout the tree. In addition to the foregoing, the fruit of the new peach tree also appears to have good handling and shipping qualities.

The 'Burpeachtwentysix' peach tree bears fruit which are ripe for commercial harvesting and shipment on approximately August 10 to August 17 under the ecological conditions prevailing in the San Joaquin Valley of central California. In relative comparison to the 'Burpeachfour' peach tree (U.S. Pat. No. 12,405), which produces fruit having a similar harvesting date, the new variety of peach tree bears fruit which exhibits a higher level (approximately 3-7 brix) of soluble solids than the 'Burpeachfour' when both varieties have been grown and evaluated under the same cultural conditions, and at the same geographical location. Further fruit of the subject variety generally exhibits a more oblate shape than does the 'Burpeachfour'. Further, with respect to the pollen parent (E48.050) this variety ripens about one month earlier than the present variety. Additionally, with respect to the seed parent (E62.012) this variety ripens one month later than the new variety.

BRIEF DESCRIPTION OF THE DRAWINGS

The accompanying drawing, which is provided, is a color photograph of the new peach tree variety. The photograph depicts two whole mature fruit showing the top and bottom characteristics thereof, and one mature fruit bisected laterally along the equatorial plane, and which reveals the flesh characteristics thereof. The external coloration of the fruit as shown in the photograph is sufficiently matured for harvesting and shipment. Additionally, the photograph displays a sample vegetative shoot bearing typical leaves, and a typical stone, with the flesh removed to display the surface characteristics thereof. The colors in this photograph are as nearly true as is reasonably possible in a color representation of this type. Due to chemical development, processing, and printing, the leaves and fruit depicted in this photograph may or may not be accurate when compared to the actual specimen. For this reason, future color references should be made to the color plates (Royal Horticultural Society) and descriptions provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the fourth fruiting season under the ecological conditions prevailing at the orchards of the assignee which are located near the town of Fowler, county of Fresno, state of California. All major color code designations are by reference to The R.H.S. Colour Chart (Fourth Edition) provided by The Royal Horticultural Society of Great Britain. Common color names are also occasionally used.

TREE

Size: Generally. Considered medium to medium large as compared to other common commercial peach cultivars ripening in the late season of maturity. The trees of the present variety were pruned to a height of approximately 280.0 cm to about 300.0 cm at commercial maturity.

Vigor: Considered vigorous. The present peach tree variety grew from about 170.0 cm to about 175.0 cm in height during the first growing season. The new variety was pruned to a height of approximately 160.0 cm during the first dormant season, and primary scaffolds were then selected for the desired tree structure.

Productivity: Productive. Fruit set varies from more than the desired crop load to levels much higher than desired levels when grown in a suitable horticultural zone, and under normal commercial conditions. The fruit set is spaced by selective thinning to develop the remaining fruit into the desired market-sized fruit. The number of the fruit set varies with the prevailing climatic conditions and cultural practices. Therefore, productivity is not a distinctive characteristic of the new variety.

Fruit bearing: Regular. Fruit set has been above average during the previous years of observation, and thinning was necessary during the past 4 years on both the original seedling and on subsequently asexually produced trees.

Form: Upright, and pruned into a vase shape.

Density: Considered moderately dense. It has been discovered that pruning the branches from the center of the trees to obtain a resulting vase shape allows for air movement and appropriate amounts of sunlight to enhance fruit coloration, and renewal of fruiting wood throughout the tree.

Hardiness: The present tree was grown and evaluated in USDA Hardiness Zone 9. The calculated winter chilling requirements of the new tree is approximately 550 hours at a temperature below 7.0 degrees C. The present variety appears to be hardy under typical central San Joaquin Valley climatic conditions.

TRUNK

Diameter: Approximately 12.5 cm in diameter when measured at a distance of approximately 15.24 cm above the soil level. This measurement was taken at the end of the fourth growing season.

Bark texture: Considered moderately rough, with numerous folds of papery scarfskin being present. Since bark development and coloration change with the tree age this characteristic varies with tree vigor, age and regional environmental conditions, and therefore is not a dependable descriptor of the variety.

Lenticels: Numerous flat, oval lenticels are present. The lenticels range in size from approximately 4.0 millimeters to about 6.0 mm in width, and between about 1.0 and about 2.0 millimeters in height. The development and size of the trunk lenticels can be influenced, to some degree, by the ambient growing conditions, and are not, necessarily, a dependable characteristic of this variety. As trees of this variety mature, lenticels are present but are generally covered by increasing layers of cork (mature bark) and therefore are less apparent.

Lenticel color: Considered an orange brown, (RHS Greyed-Yellow Group 162 C).

Bark coloration: Variable, but it is generally considered to be a medium brown, (RHS Greyed-Orange Group 166 B). This bark description was taken from trees in their fifth leaf which have not yet ruptured the scarf skin, nor developed bark furrowing which is much more typical of the bark of older trees. It should be noted that the coloration of the bark varies as the smoother, darker background color approaches other bark features such as the bark lenticels and the initial fissures which become present during scarf skin development.

BRANCHES

Size: Considered medium for the variety.

Diameter: Average as compared to other peach varieties. The branches have a diameter of about 7.5 centimeters when measured during the fourth year after grafting.

Surface texture: Average, and appearing furrowed on wood which is several years old.

Crotch angles: Primary branches are considered variable, and are usually growing at an angle of about 51 to about 58 degrees when measured from a horizontal plane. This particular characteristic is not considered distinctive of the variety as this characteristic can be influenced, to some degree, by tree vigor, rootstock and other cultural conditions.

Current season shoots: Surface texture—Substantially glabrous.

Internode length: Approximately 2.5 cm.

Color of mature branches: Grey brown, (RHS Grey-Brown Group N199 D).

Current seasons shoots: Color.—Medium-light green, (RHS Green Group 143 B). The color of new shoot tips is considered a bright and shiny green (RHS Green Group 143 A). The vegetative shoot color can be significantly influenced by plant nutrition, irrigation practices and exposure to sunlight, and therefore should not be considered a consistent botanical characteristic of this variety.

LEAVES

Size: Considered medium for the species. Leaf measurements have been taken from vigorous, upright, current-season growth, at approximately mid-shoot. It should be understood that the leaf size is often influenced by prevailing growing conditions, the amount of sunlight, and the location of the leaf within the tree canopy. For this reason, leaf sizes can vary significantly based upon the factors listed above and are not typically considered a dependable botanical descriptor. Leaf bud burst typically occurs about March 8-10 under typical cultural conditions.

Leaf length: Approximately 150.0 to about 170.0 millimeters.

Leaf width: Approximately 27.0 to about 33.0 millimeters.

Leaf base-shape: The leaves generally exhibit equal marginal symmetry relative to the leaf longitudinal axis.

Leaf form: Lanceolate.

Leaf tip form: Acuminate.

Leaf color: Upper Leaf Surface—Dark green, (approximately RHS Green Group 131 B).

Leaf texture: Glabrous.

Leaf color: Lower Surface—Deep green, (approximately RHS Yellow-Green Group 146 B).

Leaf venation: Relatively broadly pinnately veined.

Mid-vein: Color.—Considered a light yellow-green, (approximately RHS Yellow-Green Group 150 C) in the early to mid period of the growing season.

Leaf margins: Gently undulating.

Form: Considered bluntly serrate, occasionally biserrate.

Uniformity: Considered generally uniform.

Leaf petioles:

*Form.*—Considered canaliculate but having a shallow channel and more pronounced trough from the dorsal aspect. Rounded from the ventral aspect.

*Size.*—Considered medium large for the species.

*Length.*—About 9.0 to about 11.0 mm.

*Diameter.*—About 1.5 to about 2.0 mm.

Color: Pale green, (approximately RHS Yellow-Green Group N144 C).

Leaf glands:

*Size.*—Considered small for the species; approximately 1.0 mm in length, and about 1.0 mm in height.

*Number.*—Generally one to two glands per marginal side are found. Observations of more than two glands per marginal side are more uncommon.

*Type.*—Generally considered to be a tight, small reniform shaped gland.

*Color.*—Considered a pale green, approximately (RHS Green Group 143 B). Typically the coloration of the glands darkens and occasionally begins to desiccate during and after the mid-late growing season.

Leaf stipules:

*Size.*—Medium large for the variety.

*Number.*—Typically 2 per leaf bud, and up to 6 per shoot tip.

*Form.*—Lanceolate in form and having a serrated marginal edge.

*Color.*—Green, (approximately RHS Green Group 137 A) when young, but graduating to a brown color, (approximately RHS Greyed-Orange group 164 C) with advancing senescence. The leaf stipules are generally considered to be early deciduous.

FLOWER

Flower buds: Hardiness.—No winter injury (bud death) has been noted during the last several years of observation in the central San Joaquin Valley. The new variety of peach tree has not been intentionally subjected to drought or heat stress, and therefore this information is not available.

Date of first bloom: Observed on Feb. 24, 2010. Flower bud color at slight bud swell is reddish-purple (RHS Grey-purple 183C).

Blooming time: Considered medium in relative comparison to other commercial peach cultivars grown in the central San Joaquin Valley. The date of full bloom was observed on Feb. 30, 2010. The date of full bloom varies slightly with climatic conditions, and prevailing cultural practices. The bloom has a slight pleasant fragrance.

Duration of bloom: Approximately 9 days. This characteristic varies slightly with the prevailing climatic conditions.

Flower type: The variety is considered to have a showy type flower.

*Flower petals.*—About 17-21 mm. in length; About 14-18 mm. in width; Ovoid in shape;

*Marginal form.*—Undulating;

*Color.*—Light pink (RHS Red-purple group 65C); An apical groove is typically present;

*Petal claw shape.*—Triangular; Width — 7.0-9.0 mm.; Length — 10-12 mm.;

*Flower pedicel.*—Length — About 4.0-5.0 mm.; Width — about 2.0-2.5 mm.;

*Color.*—Dull green (RHS Green group 143B) when bud scales are removed.

Bloom quantity: Considered abundant.

*Floral nectarines.*—Color — Deep grey-orange (RHS Grey-orange group N167B).

Flower bud frequency: Normally two flower buds appear per node, occasionally one, rarely more than two.

*Pollen Production—Abundant.*

*Pollen Color.*—(RHS Yellow-orange group 17B.

*Fertility.*—Self fertile.

Petal count: Nearly always 5.

*Calyx.*—Size — About 6-8 mm. in width; about 10 mm. in length; conical in shape;

*Color.*—Dull purple (RHS Grey-purple group N186C).

Anthers:

*Generally.*—Medium to small for the species.

*Color.*—Dull red/purple, approximately (RHS Greyed-Red Group 179A).

Filiments:

*Size.*—Variable in length, approximately 15.0 to 17.0 millimeters in length;

*Color.*—Considered a medium to pale pink, (RHS Red-Purple Group 65 C).

Pistil:

*Number*.—Usually 1, rarely 2;

*Generally*.—Medium in size;

*Length*.—Approximately 16.0-18.0 millimeters in length including the ovary;

*Color*.—Considered a pale green, (approximately RHS Yellow-Green Group 145 C); and

*Surface texture*.—The variety has a long pubescent pistil.

FRUIT

Maturity when described: Firm ripe condition (shipping ripe).

Date of first picking: Aug. 10, 2010. Date of last picking. — Aug. 17, 2010. The date of harvest varies slightly with the prevailing climatic conditions and cultural practices.

Size: Generally—Considered large, and uniform.

Average cheek diameter: Approximately 68.0 to about 79.0 millimeters, and sometimes larger.

Average axial diameter: Approximately 62.0 to about 68.0 millimeters, and sometimes larger.

Typical weight: Approximately 278.0 grams. This characteristic is quite dependent upon the prevailing cultural practices, and therefore is not particularly distinctive of the new variety.

Fruit form: Generally—Considered slightly oblate. The fruit is generally uniform in symmetry.

Fruit suture: No apparent protrusion, callousing or stitching exists along the suture line.

Suture: Color—Generally blushed to the same degree as the skin, (approximately RHS Red Group 42 A).

Ventral surface: Form—Quite even and uniform in appearance when viewed from the lateral sutorial plane.

Apex: Generally-Rounded.

Base: Shape—Gently refuse.

Stem cavity: Generally—Rounded and uniform in shape. The average depth of the stem cavity is about 7.0 mm. Average width of the stem cavity is about 12.0 mm. Average length of the in the sutorial plane is about 20.0 mm.

Fruit skin:

*Thickness*.—Considered medium in thickness, and tenacious to the flesh.

*Surface texture*.—Short, fine and pubescent. The pubescence is moderately abundant.

*Taste*.—Non-astringent.

*Tendency to crack*.—Not observed in the current or previous years of evaluation.

Fruit skin color:

*Blush color*.—Generally speaking, a red blush exists on a majority of the skin of the fruit (approximately RHS Orange-Red Group N34 A), and is typically more present on the portions of the fruit facing the sunlight. The blush covers approximately 70-80% of the fruit skin surface. The percentage of the blush on the fruit skin surface can vary, and is generally dependent upon the fruit's exposure to direct sunlight; specific fruit maturity; and also the prevailing ecological and cultural conditions under which the fruit is grown. It should noted that the presence of darker pigmentation 'striping' or 'tigering' is generally observed laterally, above the equatorial plane and generally increases in frequency in progression toward the fruit's apex. This additional pigmentation generally deepens the hue of the surrounding surface.

*Ground color*.—Yellow, (approximately RHS Yellow-Orange Group 21 D). The ground color of the fruit can vary significantly based upon the maturity of the fruit when this measurement is taken.

Fruit stem:

*Size*.—Medium in length, approximately 6.0 to about 9.0 millimeters.

*Diameter*.—Approximately 2.0 to about 3.0 millimeters.

*Color*.—Pale yellow-green, (approximately RHS Yellow-Green Group N144 B). Occasionally 'stem tear' (skin of the fruit, when picked, partially detaches from the flesh leaving a loose flap of skin at the base of the stem well/hilum interface) can be observed.

Fruit flesh:

*Ripening*.—Considered even.

*Texture*.—Firm, juicy and dense. Considered non-melting.

*Fibers*.—Few are found.

*Aroma*.—Slight.

*Eating quality*.—Considered very good.

*Flavor*.—Considered very sweet and with moderate to low acidity. The flavor is considered both pleasant and balanced.

*Juice production*.—Moderate.

*Brix*.—About 15.0 to 20.0 degrees. This characteristic varies slightly with the number of fruit per tree; the maturity of fruit when harvested; the prevailing cultural practices; and the ambient climatic conditions. This brix is 3-7 brix higher than fruit produced by U.S. Plant Pat. No. 12,405 when grown under the same growing conditions.

*Flesh color*.—Is considered an orange-yellow, (approximately RHS Yellow-Orange 16 A). It should be noted that the flesh can develop a reddish color at the outer margin of the pit cavity that can radiate into the flesh. This deepening color generally occurs as the fruit increasingly matures, but it is not distinctive of the variety.

STONE

Type: Considered freestone.

Size: Considered medium-large for the variety. The stone size varies significantly depending upon the tree vigor, crop load and prevailing growing conditions.

Length: Average, about 34.0 to about 41.0 millimeters.

Width: Average, about 27.0 to about 36.0 millimeters.

Diameter: Average, about 18.0 to about 24.0 millimeters.

Form: Roughly acuminate.

Base: The stone is quadrate in shape at the basal axis.

Apex: Shape.—The stone exhibits a slight to prominently acute apex.

Stone surface:

*Surface texture*.—Considered relatively course. Surface pitting is generally more noted toward the dorsal edges of the stone.

*Ridges*.—Ridging is generally more prominent and is usually oriented parallel, and laterally relative to the ventral margin.

*Ventral edge*.—The ventral edge is generally considered troughed with two reasonably distinguished edges running parallel to, and on both sides of, the stone's suture. These distinct edges continue from the hilum to the apex.

*Dorsal edge.*—Shape — Generally considered moderately rough and uneven. The folds of the surface ridges appearing on the external margins often end abruptly along the external margin of the dorsal surface creating an irregular edge. There is often substantial lobbing or a pronounced extension of the dorsal margin at its mid-point in length.

Stone color: The color of a mature, dry stone is generally considered a reddish brown, approximately (RHS Greyed-Purple Group N186 C). This depends, to some degree, on the moisture content of the stone. This color is variable, however, and may also be affected by oxidation and sun bleaching.

Tendency to split: Splitting has rarely been noted.

Kernel:

*Size.*—The kernel is considered medium-small in size.

*Form.*—Considered generally ovoid.

*Pellicle.*—Slightly pubescent.

*Color.*—(RHS Greyed-Orange Group N167 B).

Use: The present variety 'Burpeachtwentysix' is considered to be a peach tree of the late season of maturity, and which produces fruit which are considered to be firm, attractively colored, and which are useful for both local and long distance shipping.

Keeping quality: Appears excellent. The fruit of the present variety has stored well for up to 30 days after harvest at 1.0 degree Celsius.

Shipping quality: Good. The fruit of the new peach tree variety showed minimal bruising of flesh or skin damage after being subjected to normal harvesting and packing procedures.

Resistance to insects and disease: No particular susceptibilities were noted. The present variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control, frost, climatic variables and horticultural management are to be expected.

Having thus described and illustrated our new variety of peach tree, what we claim is new, and desire to secure by Plant Letters Patent is:

1. A new distinct variety of peach tree, substantially as illustrated and described, and which is characterized principally as to novelty by producing an attractively colored yellow-fleshed, freestone peach which is mature for harvesting and shipment approximately August 10 to August 17 under the ecological conditions prevailing in the San Joaquin Valley of central California.

* * * * *

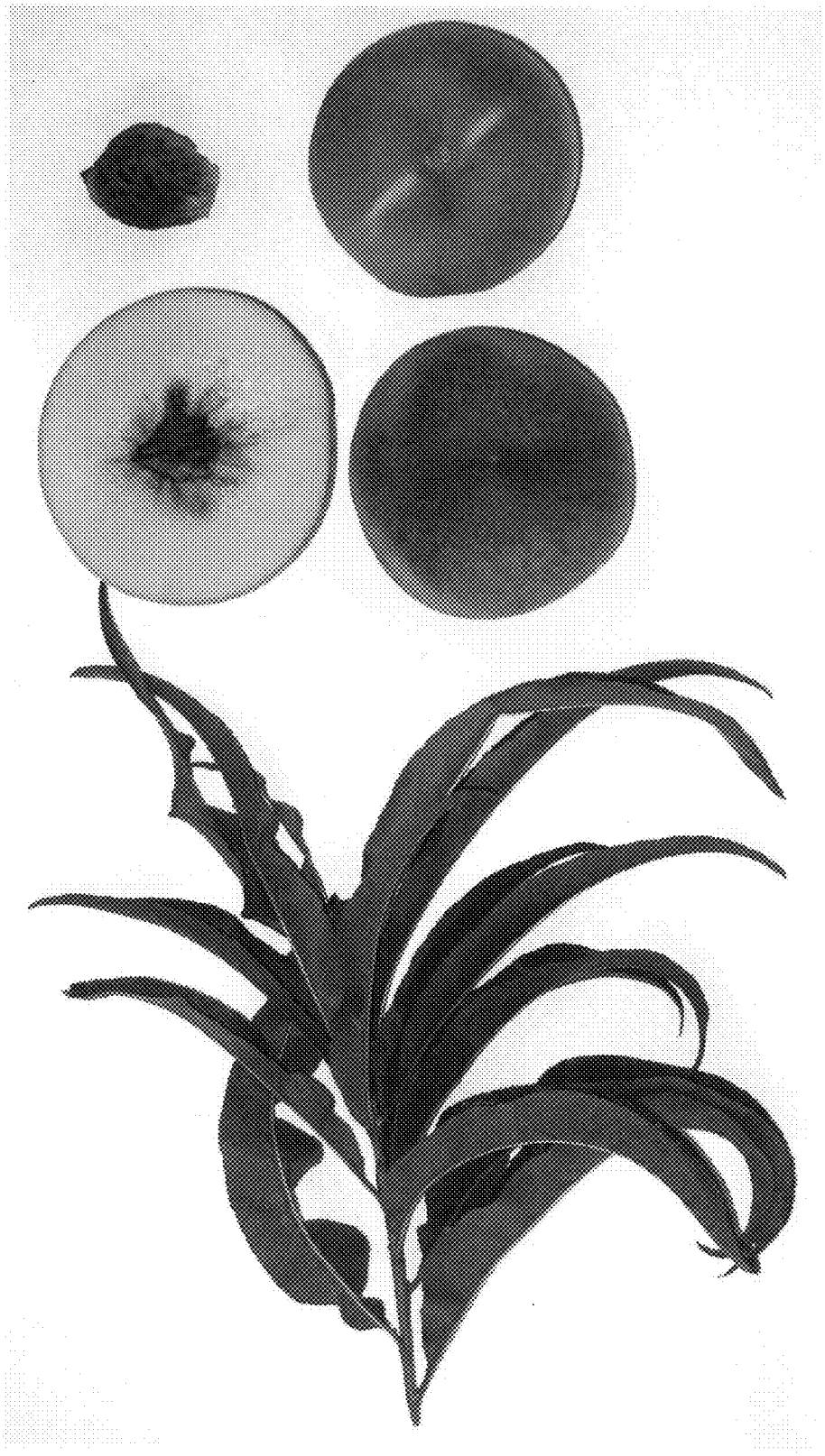

UNITED STATES PATENT AND TRADEMARK OFFICE

CERTIFICATE OF CORRECTION

PATENT NO. : PP23,161 P3
APPLICATION NO. : 12/928629
DATED : November 6, 2012
INVENTOR(S) : John K. Slaughter et al.

It is certified that error appears in the above-identified patent and that said Letters Patent is hereby corrected as shown below:

Title Page: Column 1, line 4, please replace "The present invention relates to a new and distinct variety of distinct variety of..."

with --The present invention relates to a new and distinct variety of...--

Signed and Sealed this
First Day of January, 2013

David J. Kappos

David J. Kappos
*Director of the United States Patent and Trademark Office*